July 15, 1969 J. R. LARUS ET AL Plant Pat. 2,905
GLADIOLUS PLANT
Filed Nov. 24, 1967
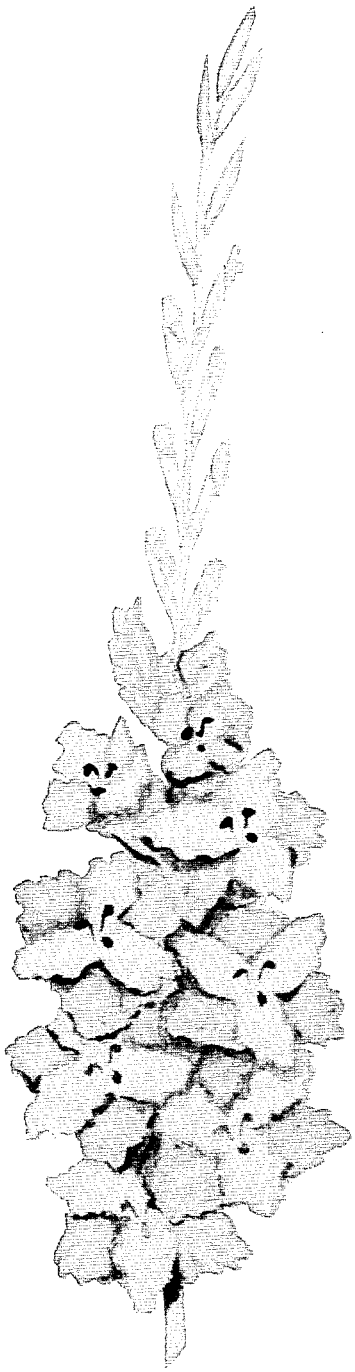
INVENTOR
Charles T. Larus
John R. Larus
By: Lamont Johnston
ATTORNEY United States Patent Office Plant Pat. 2,905
Patented July 15, 1969

2,905
GLADIOLUS PLANT

John R. Larus, West Hartford, and Charles T. Larus, Avon, Conn., assignors to Selected Glads, Inc., New Albany, Ind., a corporation of Tennessee Filed Nov. 24, 1967, Ser. No. 685,719
Int. Cl. A01h 5/02
U.S. Cl. Plt.—85 1 Claim Our invention relates to a new and improved variety of gladiolus plant, notable particularly for the intense, deep color of its blossom and for its robust vigor and ability to perform well in all parts of the United States. We have identified this new variety as seedling #56-35-C in our breeding work.

To the best of our knowledge, this variety is the result of a cross between Royal Stewart (Plant Patent No. 1,339), and Burma (unpatented). Royal Stewart was the seed parent and Burma the pollen parent. Hand cross pollination was done by us in our field at Avon, Conn., but no precaution was taken to prevent admixture by bees or insects.

This new variety has been asexually reproduced by us in Connecticut by natural increase from cormels through several generations and its characteristics have proven to be permanently fixed.

The illustration, made a part of this application, shows a single bloom spike, reduced in size. The illustration shows the form and placement of the florets on the spike and is as nearly true to color as it is possible to depict. In the following detailed description, color plate references are to "The Horticultural Colour Chart" by the British Colour Council. Where there are other references to color, the ordinary dictionary meanings of the terms are intended.

The plant

Growth: Strong; attains a height of 60 inches, overall. Fine propagator.

Blooming: Blooms in 75 days from large bulbs in the North.

Stems: Diameter of stem is ½ inch. Color of stem above the bulb is purple.

Foliage: Deep green and semi-drooping. Leaves are 1½ inches across.

Disease resistance: Excellent resistance to known gladiolus diseases.

Corms: Round and high-crowned, with excellent husk coverage. Husk has a purple cast. Color of flesh is yellow.

The flower

Spike: Flowerhead is 26 inches in length with twenty to twenty-two buds of which seven to eight open at one time.

Bud:

*Size.*—Opening buds are 2½ inches long.

*Opening.*—Eight show color at one time.

Flower: Florets are formally placed on the spike. Individual florets are 4½ inches across. The form is ruffled and triangular. Keeping qualities are excellent.

Petals: The shape is frilled and rounded. Upper petals are 2½ inches across; lip, 1 inch. Substance is firm. There is no fragrance. Color—Cardinal Red 822/1 shading to 822/3 at base of upper petal. Lower lip petal 822.

Reproductive organs:

*Stamen.*—Light purple.

*Pistil.*—Red.

Comparisons

Our new variety resembles no other variety because no other variety has the intensity of color that ours has.

Having thus disclosed our invention, we claim:

1. The new and improved variety of gladiolus plant, substantially as herein shown and described, characterized by its rugged growth, robust vigor, intense color of blossoms and consistent performance in all parts of the United States.

No references cited.

ROBERT E. BAGWILL, Primary Examiner